(12) United States Patent
Souchay et al.

(10) Patent No.: US 9,848,838 B2
(45) Date of Patent: Dec. 26, 2017

(54) METHOD FOR IMAGING AN ORGAN AND MEDICAL IMAGING SYSTEM

(71) Applicant: GENERAL ELECTRIC COMPANY, Schenectady, NY (US)

(72) Inventors: Henri Souchay, Buc (FR); Guy Hersemeule, Buc (FR); Benedicte Grosjean, Buc (FR); Yana Popova, Buc (FR); Mireille Haddad, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/737,327

(22) Filed: Jun. 11, 2015

(65) Prior Publication Data

US 2016/0000386 A1    Jan. 7, 2016

Related U.S. Application Data

(63) Continuation of application No. 13/473,161, filed on May 16, 2012, now abandoned.

(30) Foreign Application Priority Data

May 16, 2011 (FR) ..................... 11 54234

(51) Int. Cl.
| | |
|---|---|
| *A61B 6/04* | (2006.01) |
| *A61B 6/02* | (2006.01) |
| *A61B 6/00* | (2006.01) |
| *A61B 90/30* | (2016.01) |
| *A61B 6/08* | (2006.01) |

(52) U.S. Cl.
CPC ............ *A61B 6/0414* (2013.01); *A61B 6/025* (2013.01); *A61B 6/502* (2013.01); *A61B 6/547* (2013.01); *A61B 90/30* (2016.02); *A61B 6/08* (2013.01)

(58) Field of Classification Search
CPC ......... A61B 6/025; A61B 6/0414; A61B 6/08; A61B 6/502; A61B 6/547
See application file for complete search history.

(56) References Cited

U.S. PATENT DOCUMENTS

| | | |
|---|---|---|
| 5,872,828 A | 2/1999 | Niklason et al. |
| 6,885,724 B2 | 4/2005 | Li et al. |

(Continued)

FOREIGN PATENT DOCUMENTS

FR         2872659 A1    1/2006

OTHER PUBLICATIONS

Unofficial translation of French Search Report and Written Opinion issued in connection with corresponding FR Application No. 1154234 dated Jan. 18, 2012.

(Continued)

*Primary Examiner* — Glen Kao

(57) ABSTRACT

A method for imaging an organ with a medical imaging system comprising a radiation source, a detector facing the radiation source, an organ support and a compression paddle, wherein the compression paddle is smaller than the detector, the method comprising offsetting the compression paddle to a position towards a side edge of the detector, moving the radiation source along a trajectory, wherein the trajectory is above the compression paddle and dependent upon the position of the compression paddle, and acquiring images of the organ at several positions along the trajectory.

15 Claims, 3 Drawing Sheets

(56) References Cited

U.S. PATENT DOCUMENTS

| | | |
|---|---|---|
| 7,583,786 B2 | 9/2009 | Jing et al. |
| 8,774,355 B2 | 7/2014 | Claus et al. |
| 2003/0161439 A1 | 8/2003 | Eriksson et al. |
| 2004/0101095 A1 | 5/2004 | Jing et al. |
| 2005/0063509 A1* | 3/2005 | Defreitas ............ A61B 6/0414 378/37 |
| 2006/0262899 A1 | 11/2006 | Al-Khalidy et al. |
| 2007/0183565 A1* | 8/2007 | Brandstatter ............ A61B 6/08 378/37 |
| 2008/0101537 A1 | 5/2008 | Sendai |
| 2008/0152077 A1 | 6/2008 | Ramsauer |
| 2009/0296881 A1* | 12/2009 | Hornig ................ A61B 6/502 378/37 |
| 2010/0091940 A1 | 4/2010 | Ludwig et al. |
| 2012/0027168 A1* | 2/2012 | Nakayama ............ A61B 6/502 378/37 |

OTHER PUBLICATIONS

Non-Final Rejection towards corresponding U.S. Appl. No. 13/473,161 dated Apr. 25, 2014.
Unofficial English translation of CN Office Action and Search Report issued in connection with related CN Application No. 201210253226.3 dated Feb. 12, 2015.

* cited by examiner

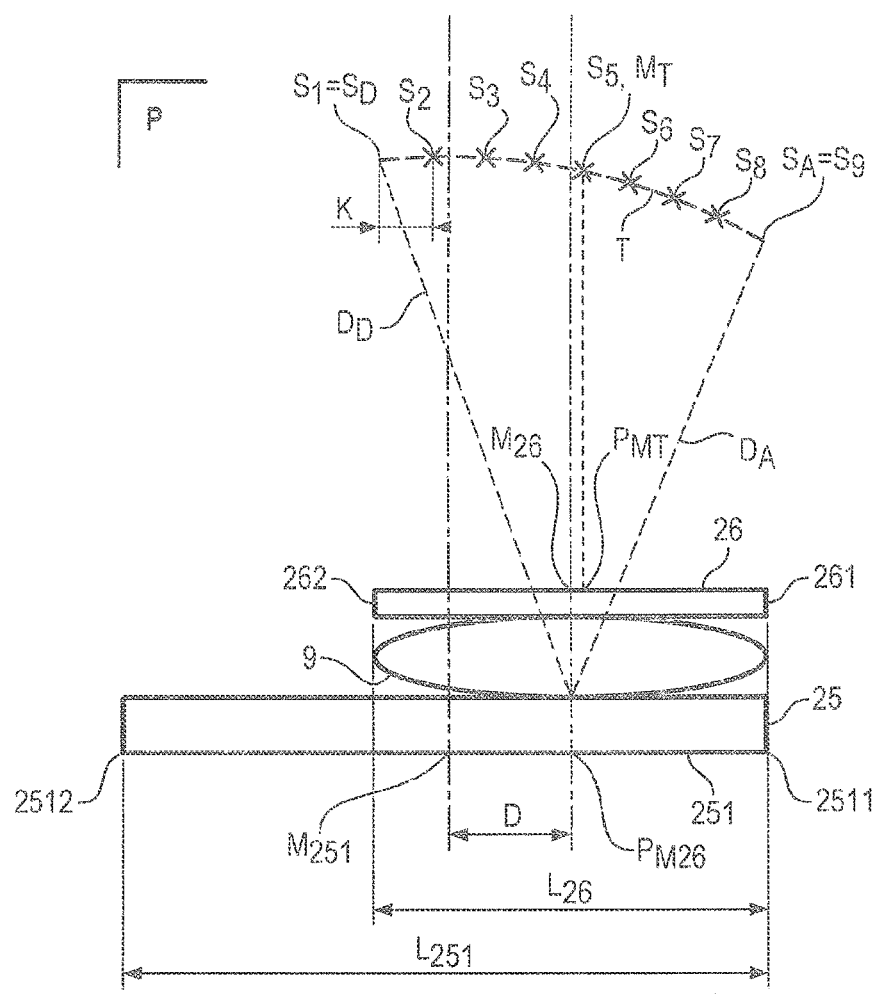

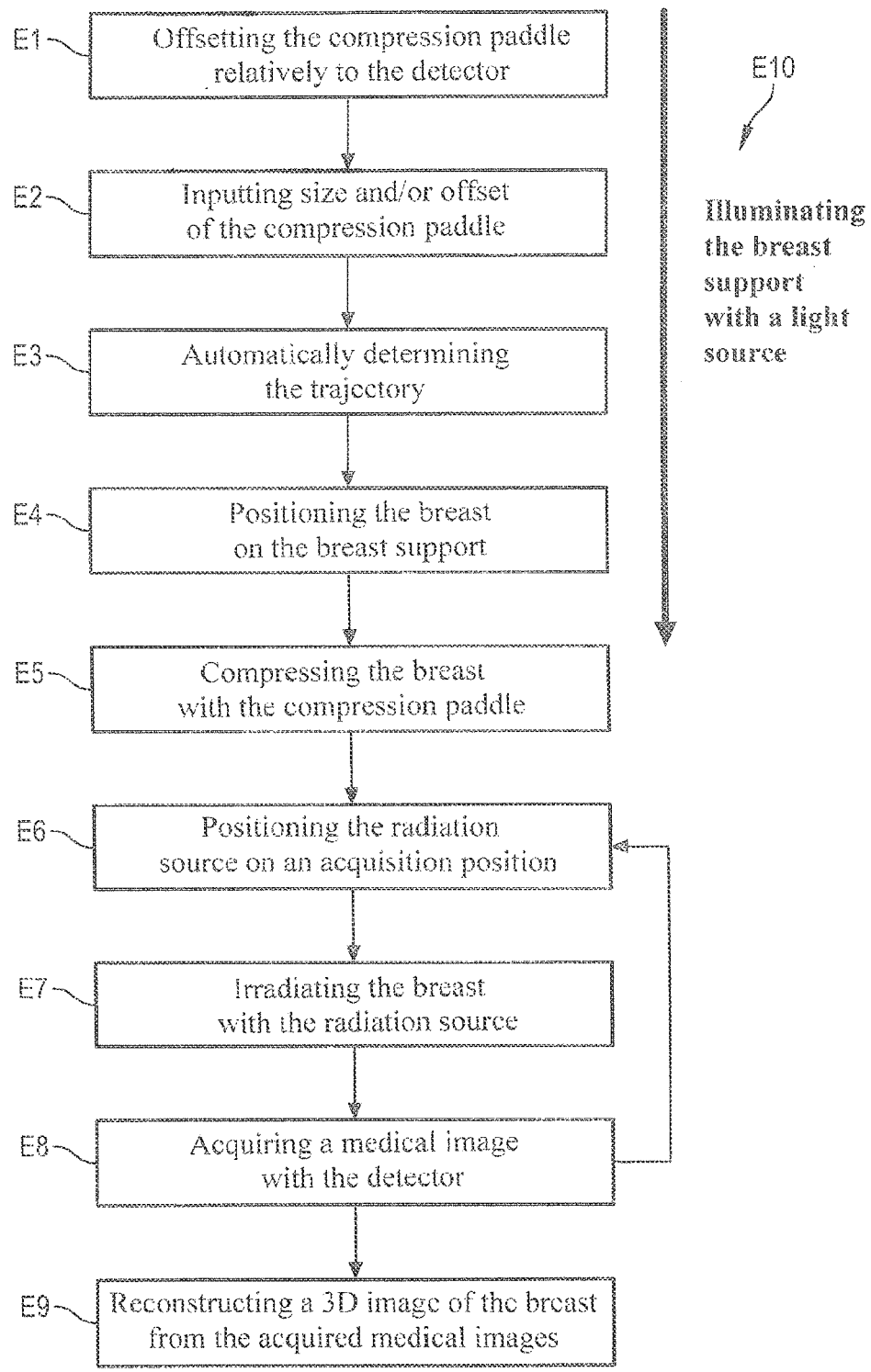

METHOD FOR IMAGING AN ORGAN AND MEDICAL IMAGING SYSTEM

CROSS-REFERENCE TO RELATED APPLICATIONS

This application is a continuation of U.S. application Ser. No. 13/473,161, filed May 16, 2012, which claims foreign priority benefits to French Application No. 1154234, filed May 16, 2011; both applications are incorporated herein by reference in their entireties.

BACKGROUND OF THE INVENTION

Field of the Invention

Embodiments of the present invention relate to the field of radiology using digital tomosynthesis and, more particularly, to methods for imaging small breasts or part of a breast.

Description of the Prior Art

Conventionally, mammography is a type of radiography wherein two-dimensional images are provided to a practitioner. A patient's breast is positioned on a breast support plate and then compressed by a compression paddle. The breast is positioned on the breast support so that the breast is fully irradiated by a radiation of an X-ray source.

Another type of breast radiography, breast radiography using tomosynthesis, provides three-dimensional images of an organ.

In breast tomosynthesis, several images of a breast held in position are acquired at different positions of an X-ray source of a medical imaging system relative to a detector. Usually, the breast is positioned on a breast support plate in which the detector of the medical imaging system is arranged. The breast is then compressed by a compression paddle. Several images are then acquired with the X-ray source moving from a starting position to a finishing position, while the breast, the support and the paddle remain in position. The X-ray source describes a movement relative to the detector. This movement is generally a rotation around a point located on a plane passing through the breast, in the center of the edge of the detector opposite to the patient.

A three-dimensional image of the breast is then reconstructed from the acquired images. Reconstruction quality depends upon the beam angle (angle between the two end positions of the source) and the number of acquired images.

In general, the frontal width of the compression paddle is substantially equal to the frontal width of the detector. However, for a small-size breast, a compression paddle with a smaller frontal width is used to facilitate positioning of the small-sized breast on the breast support.

To obtain a good quality three-dimensional image of the breast, it is important to avoid the projection of any object other than the breast to be imaged onto the detector. However, when a compression paddle with a smaller frontal width is used, the edge or edges of the compression paddle are projected onto the acquired images of the breast. This adds undesired data to the medical images.

BRIEF SUMMARY OF THE INVENTION

According to an embodiment of the present invention, there is provided a method for imaging an organ with a medical imaging system comprising a radiation source, a detector facing the radiation source, an organ support and a compression paddle, wherein the compression paddle is smaller than the detector. The method comprises offsetting the compression paddle to a position towards a side edge of the detector, moving the radiation source along a trajectory, wherein the trajectory is above the compression paddle and dependent upon the position of the compression paddle, and acquiring images of the organ at several positions along the trajectory.

According to another embodiment of the present invention, there is provided a medical imaging system. The system comprises an acquisition module comprising a radiation source configured to emit radiation towards an organ, an organ support configured to support the organ, a detector configured to capture the radiation from the radiation source that has passed through the organ, a compression paddle configured to compress the organ against the organ support, wherein the compression paddle is smaller than the detector and is offset towards a side edge of the detector, and a positioning arm configured to position the radiation source at successive acquisition positions along a trajectory, wherein the trajectory is above the compression paddle and is dependent upon the position of the compression paddle, and a control unit configured to drive the positioning arm to center the trajectory on the compression paddle.

BRIEF DESCRIPTION OF THE DRAWINGS

Features and advantages of embodiments of the present invention will become apparent on reading the detailed description below with reference to the drawings, which are illustrative but non-limiting, wherein:

FIG. 2 schematically illustrates a plane of trajectory of a radiation source of a medical imaging system according to an embodiment of the present invention; and FIG. 3 is a schematic diagram showing the steps of a method for imaging an organ according to an embodiment of the present invention.

DETAILED DESCRIPTION OF THE INVENTION

Figure 1:
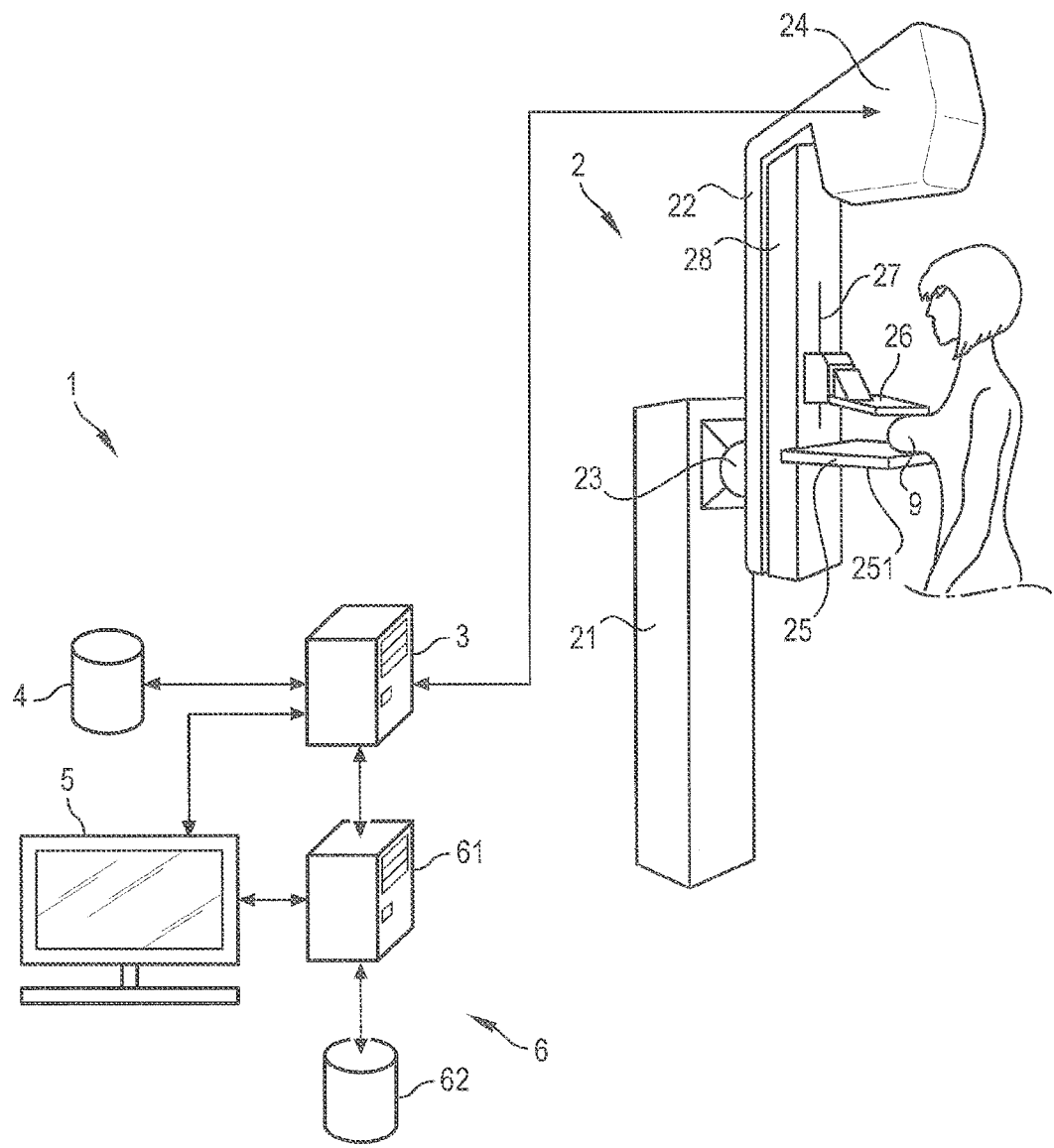
FIG. 1 illustrates a medical imaging system implementing the method for imaging an organ according to an embodiment of the present invention.

According to an embodiment, there is provided a medical imaging system.

FIG. 1 schematically illustrates a medical imaging system 1 for acquiring medical images allowing three-dimensional (3D) reconstruction of a breast 9 from two-dimensional (2D) images of the breast 9.

In one embodiment, the medical imaging system 1 may be an apparatus for mammography and, in particular, for digital breast tomosynthesis.

In one embodiment, the medical imaging system 1 comprises a module 2 for acquiring 2D images. The acquisition module 2 comprises a detector 251 facing a radiation source 24, the detector 251 is illuminated by the radiation source 24 during acquisition of medical images. The radiation source 24 is mobile relative to the detector 251. In one embodiment, the detector 251 may also be mobile relative to the radiation source 24.

The acquisition module 2 comprises, for example, a vertical stand 21 and a positioning arm 22 connected to the radiation source 24, which may be, for example, an X-ray source. In one embodiment, the acquisition module 2 further comprises a harmless light source (not shown) configured to provide illumination during positioning of the breast 9 to be imaged.

The positioning arm 22 is rotatably connected to the vertical stand 21 by a rotation shaft 23. The vertical stand 21 is fixed. Therefore, the radiation source 24 can be placed in acquisition positions by rotating the positioning arm 22.

The acquisition module 2 also comprises a supporting arm 28 comprising a platform comprising a breast support 25 and a compression paddle 26 parallel to the breast support 25, wherein the compression paddle 26 is configured to compress the breast 9 positioned on the breast support 25.

The compression paddle 26 is positioned above the breast support 25 and can be translated relative to the breast support 25 along a translation rail 27. The breast support 25 comprises a detector 251 corresponding to the radiation used by the radiation source 24. In one embodiment, the detector 251 is a radiation detector The breast support 25 and the compression paddle 26 keep the breast 9 fixed during the acquisition of medical images.

The breast support 25 and the compression paddle 26 may be planar. They may or may not be positioned parallel to the floor, for example, they may be positioned at about 45°. The supporting arm 28 can be rotatably mounted on the vertical stand 21 with the same axis of rotation as the positioning arm 22.

In one embodiment, the positioning arm 22 and the supporting arm 28 are separate, thereby allowing rotation of one arm relative to the other around the rotation shaft 23. The positioning arm 22 and the supporting arm 28 are positioned one relative to the other so that a large part of the radiation emitted by the radiation source 24 is received by the detector 251. As shown in FIG. 2, the compression paddle 26 may be smaller than the detector 251 and can be offset towards, for example, a side edge 2511 of the detector 251, so that one side edge 261 of the compression paddle 26 is on the same side of the side edge 2511 of the detector 251 towards which the compression paddle 26 is offset, and lies directly above this edge 2511 of the detector 251.

In one embodiment, the detector 251 may be a semiconductor image sensor comprising caesium iodide phosphor (scintillator) on a transistor/photodiode array in amorphous silicon. In other embodiments, the detector 251 can be CCD sensors or direct digital detectors which directly convert X-rays into electronic signals.

The detector 251 illustrated in FIG. 1 is planar and defines a planar image surface. In another embodiment, the detector 251 has a curved shape which forms a curved image surface. In another embodiment, the detector 251 moves during image acquisition.

In one embodiment, the acquisition module 2 also comprises a collimator (not shown) placed underneath the radiation source 24 to delimit the portion of space illuminated by the radiation source 24. The collimator comprises four strips which each can be moved independently. A first strip is placed between the center of rotation of the radiation source 24 and a patient's chest (the front strip). The front strip blocks part of the radiation from the radiation source 24 oriented towards the patient. A second strip (the rear strip) is placed opposite to the front strip. The rear strip blocks part of the radiation from the radiation source 24 oriented towards the front of the detector 251. Finally, two side strips block part of the radiation from the radiation source 24 that is oriented sideways.

The acquisition module 2 also comprises a light source (not shown) which can be positioned at the same acquisition positions as the radiation source 24. The light source is used to illuminate the breast support 25 and the detector 251. The collimator strips also limit the portion of space illuminated by the light source.

In one embodiment, the medical imaging system 1 also comprises a control unit 3 connected to the acquisition module 2 through a wire or network connection. The control unit 3 is designed to retrieve data relating to the size of the compression paddle 26 and/or the offset thereof relative to the detector 251.

The control unit 3 sends electric control signals to the acquisition module 2 to set several parameters such as the radiation dose to be emitted, the angular positioning of the supporting arm 28, and/or the compression force to be applied by the compression paddle 26 to the breast 9.

The control unit 3 also controls the angular positioning of the positioning arm 22 so that it causes the radiation source 24 to describe a trajectory T above the compression paddle 26. The control unit 3 is also designed to drive the positioning arm 22 to center the trajectory T on the compression paddle 26 so that, for example, the trajectory T starts at one of the end positions located directly above a side edge 261, 262 of the compression paddle 26 and finishes at the other of the end positions located directly above another side edge 261, 262 of the compression paddle 26.

The control unit 3 may comprise a reading device (not shown), for example, a diskette reader, CD-ROM, DVD-ROM reader or connection ports, for reading instructions of a processing method from an instruction medium (not shown) such as a diskette, CD-ROM, DVD-ROM, or USB key or more generally any removable memory storage or through a network connection.

In one embodiment, the control unit 3 may comprise a wire or wireless network connection device (not shown). In another embodiment, the control unit 3 executes instructions for a processing method stored in firmware.

In one embodiment, the medical imaging system 1 further comprises a memory unit 4 connected to the control unit 3 for recording parameters and acquired images. Provision may be made for the memory unit 4 to be located inside or outside the control unit 3. In one embodiment, the memory unit 4 may be formed of a hard disk or SSD, or any other removable, re-write storage means (USB keys, memory cards, etc.). In another embodiment, the memory unit 4 may be ROM/RAM memory of the control unit 3, a USB key, a memory card or memory of a central server.

In one embodiment, the medical imaging system 1 comprises a display unit 5 connected to the control unit 3 to display acquired images and/or data on parameters that the control unit 3 transmits to the acquisition module 2.

In other embodiments, the display unit 5 may be integrated in the acquisition module 2, the control unit 3, or a 3D computer 61 as described below. In one embodiment, the display unit 5 may be a separate unit such that, for example, a radiologist would have an independent viewing station with the display unit 5 to view and determine diagnosis from digital medical images.

The display unit 5 may, for example, be a computer screen, a monitor, flat screen, plasma screen or any type of commercially available display device.

The display unit 5 enables a practitioner to control the reconstruction and/or display of the acquired 2D images.

In one embodiment, the medical imaging system 1 is coupled with a computing system 6 comprising the 3D computer 61 which receives the acquired images stored in the memory unit 4 of the medical imaging system 1, which it uses to construct a 3D image of the breast by digital tomosynthesis. An example of a method for digital breast tomosynthesis is described in more detail in document FR 2 872 659, which is hereby incorporated by reference.

The 3D computer 61 is, for example, one or more computers, one or more processors, one or more microcontrollers, one or more micro-computers, one or more programmable logic controllers, one or more application-specific integrated circuits, other programmable circuits or other devices which include a computer such as a work station.

The computing system 6 also comprises a memory unit 62 for storing data generated by the 3D computer 61.

In the description of different embodiments of the present invention below, reference will be made to X-ray mammography in which case the tissue matrix is a breast. This description in no way reflects any limitation of embodiments of the present invention to the sole application to mammography. Persons skilled in the art will be able to adapt the teaching described below to any type of image acquisition technique allowing the same and to any type of tissue matrix.

According to another embodiment of the present invention, with reference to FIGS. 2 and 3, there is provided a method for imaging a breast 9 or part of a breast 9. The breast 9 is compressed between a breast support 25 and a compression paddle 26 of an acquisition module 2. The acquisition module 2 also comprises a radiation source 24 and a detector 251 placed underneath the breast support 25.

The method comprises compressing E5 the breast 9 between the breast support 25 and the compression paddle 26.

The method also comprises moving the radiation source 24 along a given trajectory T above the compression paddle 26 depending on the position of the compression paddle 26, for example, centered thereupon.

Thus, the trajectory T of the radiation source 24 is asymmetric relative to the center $M_{251}$ of the detector 251, and is substantially symmetric relative to the center $M_{26}$ of the compression paddle 26.

Medical images of the breast 9 are acquired at several positions $S_1$-$S_9$ of the radiation source 24 along the trajectory T. Two positions, called end positions, delimit the trajectory T, wherein they mark the start and finish of the trajectory T.

Such trajectory T of the radiation source 24 can be used when the breast 9 to be imaged is of small size. In one embodiment, the size $L_{26}$ of the compression paddle 26 is smaller than the size $L_{251}$ of the detector 251 to facilitate positioning the small-size breast 9, particularly, on the adjacent axillary region. Since the trajectory T of the radiation source 24 is offset from the detector 251, the side edges 261, 262 of the compression paddle 26 are not included in any of the acquired medical images. This avoids artefact formation during 3D image reconstruction of the breast 9.

One of the end positions $S_A$, $S_D$ of the radiation source 24 can be configured so that one end position $S_A$ $S_D$ is located directly above a first side edge 261, 262 of the compression paddle 26, wherein the other end position $S_A$, $S_D$ is located directly above a second side edge 261, 262 of the compression paddle 26.

The radiation emitted by the radiation source 24 is captured by a detector 251 positioned underneath the breast support 25. The compression paddle 26 is smaller than the detector 251. The dimensions to be compared with each other and to be taken into account are the front dimensions relative to the positioning of a patient. That is to say that the dimensions are taken along a direction from left to right of the patient, or vice versa.

In one embodiment, for example, if the compression paddle 26 and the detector 251 are rectangular with their length oriented in the direction from left to right of a patient, the compared dimensions are the lengths of the compression paddle 26 and of the detector 251.

In another embodiment, if the detector 251 is rectangular with the length oriented in the direction from left to right of a patient and if the compression paddle 26 is oval with its major axis oriented in the same direction, then the compared dimensions are the length of the detector 251 and the major axis of the compression paddle 26.

In one embodiment, the compression paddle 26 is offset E1 towards a side edge 2511 of the detector 251 such that the center $M_{26}$ of the compression paddle 26 is not located directly above the center $M_{251}$ of the detector 251, or more generally, such that the center $M_{26}$ of the compression paddle 26 and the center $M_{251}$ of the detector 251 do not lie on one same plane perpendicular to the detector 251.

The compression paddle 26 can be laterally offset from the detector 251 so that a side edge 261, 262 of the compression paddle 26, on the same side of the side edge 2511 of the detector 251 towards which the compression paddle 26 is offset, lies directly above this side edge 2511. Thus, a small-size breast 9 can be positioned more easily.

The offset of the compression paddle 26 may result from physical offsetting of a mounting bracket (not shown) of the compression paddle 26 connecting the compression paddle 26 to the medical imaging system 1, or from a compression paddle 26 having a non-symmetric shape relative to the mounting bracket generally positioned symmetrically relative to the detector 251.

In one embodiment, the method may further comprise automatically determining E3 the trajectory T in relation to the size of the compression paddle 26 and/or to the offset thereof relative to the detector 251. In another embodiment, the trajectory T can be input into the medical imaging system 1.

The inputting E2 of the dimension of the compression paddle 26, can be performed by identification means such as an optical system (bar code), a sensor, or radiofrequency. The offset can be provided either by a practitioner or automatically determined by the medical imaging system 1.

According to one embodiment, the trajectory T lies substantially in a plane P to acquire the medical images.

On the plane P of the trajectory T, the compression paddle 26 is offset from the center $M_{251}$ of the detector, wherein the center $M_{26}$ of the compression paddle 26 does not align with the center $M_{251}$ of the detector 251.

The method comprises positioning E4 the breast 9 on the breast support 25 and compressing E5 the breast 9 with the compression paddle 26.

The method further comprises moving E6 the radiation source 24 to at least two successive positions $S_i$, $S_{i+1}$ along the trajectory T once the breast 9 has been positioned E4 and compressed E5. This movement E6 may be continuous or of variable rate with or without halting of the radiation source 24.

The trajectory T of the radiation source 24 is offset from the center $M_{251}$ of the detector 251 so that a projection $P_{MT}$ of the center of the trajectory T onto the compression paddle 26 lies substantially in the center $M_{26}$ of the compression paddle 26. This projection $P_{MT}$ lies on the plane P of the trajectory T and is done perpendicularly to the detector 251.

In addition, this allows an angular aperture ɸ, i.e. the angle between an imaginary straight line $D_D$ passing through an orthogonal projection $P_{M26}$ of the center of the compression paddle 26 onto the detector 251 and the first acquisition position $S_D$ ("starting" position), and an imaginary straight line $D_A$ passing through the orthogonal projection $P_{M26}$ of the center of the compression paddle 26 and the last acquisition position $S_A$ (finishing" position).

In one embodiment, two successive acquisition positions $S_i$, $S_{i+1}$ of the radiation source 24 are spaced apart by a regular pitch K. In a conventional system, a trajectory is normally either distributed on both sides of a plane perpendicular to a detector, or starts more or less vertically above the center of the detector towards one edge thereof. However, in an embodiment of the present invention, each of the acquisition positions $S_1$-$S_9$ of the radiation source 24 are offset by one same integral number N of pitches K in the direction of offset of the center $M_{26}$ of the compression paddle 26 from the detector 251 and from the trajectory conventionally used.

In other words, in one embodiment, N end acquisition positions on the side 2511, 2512 opposite to the side 2511, 2512 towards which the center $M_{26}$ of the compression paddle 26 is offset are not considered, and N other acquisition positions at the end of the trajectory T on the side 2511, 2512 towards which the center $M_{26}$ of the compression paddle 26 is offset are added.

For example, if, as seen in the plane P of the trajectory T, D is the distance between the center $M_{251}$ of the detector and the orthogonal projection $P_{M26}$ onto the detector 251 of the center $M_{26}$ of the compression paddle 26, the integral number N of pitches K by which each of the acquisition positions S1-$S_9$ is offset can be determined using the following relationship:

$$D > N \cdot K \geq D - K.$$

If, for example, the center $M_{26}$ of the compression paddle 26 is offset towards the right as shown in FIG. 2, and if the trajectory T of the radiation source 24 moves from left to right, then the first N acquisition positions on the left are eliminated and N additional acquisition positions at the end of the trajectory T on the right are added, thereby extending the trajectory T on the right accordingly.

In another embodiment, if D is the distance between the center $M_{251}$ of the detector 251 and the orthogonal projection $P_{M26}$ onto the detector 251 of the center $M_{26}$ of the compression paddle 26, the integral number N of pitches K by which each of the acquisition positions $S_1$-$S_9$ is offset, can be determined with the following relationship:

$$D + K \geq N \cdot K > D.$$

In another embodiment, each acquisition position $S_1$-$S_9$ of the radiation source 24 can be offset by the distance D as defined above.

The trajectory T of the radiation source 24 can be chosen so that the starting acquisition position $S_D$ of the radiation source 24 and the finishing acquisition position $S_A$ of the radiation source 24 lie directly above the side edges 261, 262 of the compression paddle 26.

The method further comprises, in each of its positions $S_1$-$S_9$, the radiation source 24 irradiates E7 the breast 9, the detector 251 captures E8 the radiation that has passed through the breast 9, which corresponds to acquiring a medical image, and constructing E9 a 3D image of the breast 9 from the acquired medical images.

In one embodiment, the method may also comprise illuminating E10 the breast support 25 on which the breast 9 is positioned, once the trajectory T has been determined, so as to provide an exact view of a nominal field covered by the radiation emitted by the radiation source 24, thereby marking on the breast support 25 a positioning limit beyond which the breast 9 must not lie. This illumination is provided by a light source (not shown) which is positioned vertically above the center of the field covered by the radiation source 24, for example, at the acquisition position of the radiation source 24 closest to the center MT of the trajectory T.

The nominal field is the portion of space illuminated by the radiation source 24 at least at one half of its positions. For example, if the number of positions is nine, one half thereof is 4.5; hence the nominal field is illuminated by the radiation source 24 at least in five of its positions. In general, if the radiation source 24 is successively positioned at N positions for the acquisition of images, the nominal field is the portion of space illuminated by the radiation source at M positions, M being at least equal to:

$$E\left(\frac{N}{2}\right) + 1, \text{ if } N \text{ is odd; or}$$

$$E\left(\frac{N}{2}\right), \text{ if } N \text{ is even;}$$

E being the function which assumes the value of the integral part of the number to which it is applied.

Even more generally, the nominal field can be defined as the portion of space illuminated by the radiation source 24 in at least Q positions, Q being different from 1 (maximum field) and from N (optimum field).

In other embodiments, the light source illuminates the maximum field or the optimum field.

In one embodiment, the illumination is dynamic, wherein the surface of the breast support 25 which is illuminated varies according to the position of the compression paddle 26.

According to another embodiment of the present invention, with reference to FIGS. 2 and 3, there is provided a method for imaging a breast 9. The method comprises offsetting E1 the center $M_{26}$ of the compression paddle 26 relatively to the detector 251, inputting E2 to a medical imaging system 1 a size of the compression paddle 26 and/or an offset of the compression paddle 26 from to the detector 251, automatically determining E3 a trajectory T in relation to the size of the compression paddle 26 and/or the offset, for example, the trajectory T corresponds to an offset of the acquisition positions $S_1$-$S_9$ of the radiation source 24 in the direction of the offset of the center $M_{26}$ of the compression paddle 26, positioning E4 the breast 9 on the breast support 25, and compressing E5 the breast 9 with the compression paddle 26, wherein the offset is determined and controlled by the control unit 3 of the medical imaging system 1.

During steps E2-E4, the breast support 25 can be illuminated E10 by a light source. This illumination E10 may be automated, wherein the area of the breast support 25 to be illuminated varies dynamically in relation to the position of the compression paddle 26. Therefore, the position of the breast 9 on the breast support 25 can be optimized to obtain medical images not containing any data which may lead to the generation of artefacts during construction of the 3D image of the breast 9.

The method further comprises positioning E6 the radiation source 24 at the starting acquisition position $S_D$ using the positioning arm 22, irradiating E7 the breast 9 with the radiation source 24, and acquiring E8 a medical image with the detector 251.

During the acquisition E8 of the medical image, the detector 251 captures the amplitude of the radiation that has passed through the breast 9 (and through the compression paddle 26) and converts the radiation to pixels. The medical image is then recorded in the memory unit 4.

Steps E6-E8 are conducted for the successive acquisition positions by moving the radiation source 24 along the trajectory until the finishing acquisition position $S_A$ is included.

A 3D image of the breast 9 is then reconstructed E9 by the 3D computer 61 from the acquired medical images.

According to an embodiment of the present invention, the method can be implemented with a computer program comprising machine instructions when the computer program is executed or run on a computer. The program can be recorded on any suitable medium for example: hard disk, CD-ROM, DVD-ROM, diskettes, USB key, SD Card, local or remote server, etc.

What is claimed is:

1. A method for imaging an object with a medical imaging system comprising an x-ray radiation source, a detector facing the x-ray radiation source, an object support and a compression paddle, wherein the compression paddle is smaller than the detector, the method comprising:
    offsetting the compression paddle to a position towards a side edge of the detector;
    moving the x-ray radiation source along a trajectory dependent upon the position of the compression paddle between a first position aligned with a first side edge of the compression paddle and a second position aligned with a second opposing side edge of the compression paddle; and
    acquiring images of the object at several positions along the trajectory.

2. The method according to claim 1, wherein the trajectory comprises a first end position located directly above the first side edge of the compression paddle and a second end position located directly above the second side edge of the compression paddle.

3. The method according to claim 1, wherein an edge of the compression paddle lies directly above the side edge of the detector towards which the compression paddle is offset.

4. The method according to claim 1, further comprising:
    inputting a dimension of the compression paddle and/or a dimension of the offset of compression paddle relative to the detector into the medical imaging system; and
    automatically determining the trajectory in relation to the dimension of the compression paddle and/or the dimension of the offset of the compression paddle relative to the detector.

5. The method according to claim 1, wherein the medical imaging system further comprises a light source positioned in a center of a field covered by the radiation source, the method further comprising:
    positioning the object on the object support; and
    marking a positioning limit on the object support, wherein the object lies within the positioning limit.

6. The method according to claim 1, wherein the trajectory is asymmetric relative to the center of the detector and substantially symmetric relative to the center of the compression paddle.

7. The method according to claim 1, wherein the center of the trajectory lies substantially in the center of the compression paddle.

8. The method according to claim 1, further comprising acquiring a medical image at each of the first position and the second position.

9. A medical imaging system comprising:
    an acquisition module comprising:
        an x-ray radiation source;
        an object support;
        a detector configured to capture the radiation from the x-ray radiation source that has passed through the object;
        a compression paddle configured to compress the object against the object support, wherein the compression paddle is smaller than the detector and is offset towards a side edge of the detector; and
        a positioning arm configured to position the x-ray radiation source at successive acquisition positions along a trajectory, wherein the trajectory is dependent upon the position of the compression paddle; and
    a control unit configured to drive the positioning arm so that the trajectory starts at a position aligned with a first side edge of the compression paddle and finishes at another position aligned with a second opposing side edge of the compression paddle.

10. The medical imaging system according to claim 9, wherein the control unit is configured to drive the positioning arm so that the trajectory starts directly above the first side edge of the compression paddle and finishes directly above the second side edge of the compression paddle.

11. The medical imaging system according to claim 9, wherein an edge of the compression paddle is on the same side of an side edge of the detector towards which the compression paddle is offset, and lies directly above the side edge of the detector.

12. The medical imaging system according to claim 9, wherein the control unit is further configured to retrieve data on the size of the compression paddle and/or on the offset of the compression paddle relative to the detector.

13. A medical imaging system comprising:
    an x-ray radiation source;
    an object support;
    an x-ray detector adjacent the object support;
    a compression paddle configured to compress an object against the object support; and
    a positioning arm configured to position the x-ray radiation source at successive acquisition positions along a trajectory, the trajectory dependent upon the position of the compression paddle and defining a first end position aligned with a first side edge of the compression paddle and second end position aligned with a second side edge of the compression paddle, said first and second side edges being opposing outer edges of the compression paddle.

14. The medical imaging device of claim 13, farther comprising a control unit configured to control movement of the positioning arm along the trajectory.

15. The medical imaging device of claim 14, wherein the control unit is further configured to center the trajectory on the compression paddle.

* * * * *